United States Patent [19]

O'Hare

[11] Patent Number: 4,833,293
[45] Date of Patent: May 23, 1989

[54] PLASMA NITROGEN FIXATION WITH SHORT PATH HEAT TRANSFER

[76] Inventor: Louis R. O'Hare, 6101 Sequoia, NW. Apt. A-20, Albuquerque, Minn. 87120

[21] Appl. No.: 121,116

[22] Filed: Nov. 16, 1987

[51] Int. Cl.[4] .............................................. B23K 9/00
[52] U.S. Cl. ........................ 219/121.48; 219/121.52; 219/121.54; 219/121.55; 219/121.36
[58] Field of Search ...................... 219/121.48, 121.49, 219/121.51, 121.52, 121.54, 121.55, 121.36, 74, 75; 313/231.31, 231.41, 231.51

[56] References Cited

U.S. PATENT DOCUMENTS 3,832,513  8/1974  Klasson ......................... 219/121.57
4,125,754  11/1978 Wasseman et al. ............ 219/121.48
4,324,971  4/1982  Frappier ......................... 219/121.57

Primary Examiner—M. H. Paschall

[57] ABSTRACT

In this invention the fixation of nitrogen by means of an electric plasma is made more energy efficient by the transfer of heat energy rapidly and directly from the product gases of the plasma to the reactant gases entering the plasma thereby rapidly cooling the combined nitrogen products and freezing the equilibrium proportions of the products found in the plasma while using the heat removed from the products to assist in heating the reactants to plasma temperature to thereby conserve a portion of the electric energy otherwise required for heating reactants, the rapid and direct transfer of heat from the product mixture leaving the plasma to the reactant mixture entering the plasma being accomplished by a gas flow through the plasma that repeatedly reverses direction anbd by multipurpose electrodes having large internal surface area and other heat transfer characteristics whereby each electrode alternately absorbs heat from drawn in plasma gas and then transfers heat to reactant gas which it subsequently directs into the plasma region, the function of each electrode during each of two alternate periods being opposite that of the other electrode in that the function of each electrode is determined by the periodic direction of gas flow from one electrode to the other through the plasma, an electrode being a cooleer of product gas and an absorber of plasma heat when downstream to the reversible gas flow and then in a subsequent period functioning to give up its absorbed heat to reactant gases when it is upstream to the flow through the plasma. The preheating of reactants and the cooling of products by this double heat transfer that takes place at the very boundaries of the plasma itself increases energy efficiency and product yield.

9 Claims, 3 Drawing Sheets

PLASMA NITROGEN FIXATION WITH SHORT PATH HEAT TRANSFER

BACKGROUND OF THE INVENTION

This invention is a type of nitrogen fixation system which employs an electric discharge through nitrogen gas and other gas such as oxygen in order to heat and to electrically activate these gases to thereby chemically react these gases into compounds of nitrogen. The reactant gases combine more readily at the high temperatures that are present in electric arcs and this invention resembles a wide variety of inventions that employ electric arcs to provide reaction products of nitrogen combined with other elements. Since the proportions of combined nitrogen products is high relative to the proportions of reactants the higher the temperature, this invention employs the type of discharge that maintains a relatively high temperature. However, this invention is not characterized as distinctive by the high temperature of its plasma since the energy requirements of achieving very high temperatures exceed the increase in yield of product at those temperatures. The invention does resemble previous systems using special means to rapidly cool the products after the gases pass through the arc. Rapid cooling is desireable because a slow cooling causes the ratio of products to reactants to adjust to the less favorable equilibrium proportions of lower temperatures as the gases pass through the lower temperature regions as they are being cooled. Many fixation processes of the past employed various types of rapid cooling in order to keep the equilibrium proportions found at the temperatures of the arc. One method of rapid cooling to "freeze the equilibrium" of the proportions found in the arc was to expose a large multiplicity of small arcs to cool, surrounding air so that the product gases in the arc would be quickly cooled by exposure to the ambient air. Rapid starting and stopping of electric arcs and sparks was another method of historical interest.

SUMMARY OF INVENTION

In this respect the present invention most closely resembles the Wielgolaski furnace process which used cooling pipes in order to quickly cool gases from an electric arc furnace. Similar examples are the Birkeland-Eyde process and the Schoenherr-Hessberger process. In the present invention, however, the hot gases from the arc are not impinged against water cooled pipes at a distance from the arc itself but rather they are moved through the very electrodes that are producing the arc and are within the arc itself. In this way any areas of slow or gradual cooling are obviated because the very hottest gases are removed directly from the plasma itself and cooled within the electrode in immediate proximity to the plasma. The electrode is uniquely configured to provide a diffused plasma and to provide a large surface area for plasma gas cooling. Also the electrodes are uniquely configured to be very rapidly cooled by reactant gases entering the plasma region. But, not only do the same electrodes provide the advantages of a diffused plasma with immediate extraction and cooling of the plasma product but they also provide a very efficient means for preheating the reactant gases and of thereby conserving and utilizing residual plasma heat. Each electrode is so configured that plasma state gases are drawn into a large multiplicity of ducts which form the electrodes' electrically active surface. By drawing the plasma into the small openings at the ends of the ducts the plasma is drawn out over a relatively large volume toward a large area of electrode. The diffusing out of the plasma assures that the energy density of the plasma will be consistant with plasma temperatures at which product is generated at the best energy efficiency. The very large surface area immediately within the ducts that form each electrode assure the quickest possible heat transfer from the plasma gas and a very quick equilibrium freeze. This same electrode structure also provides a rapid and efficient transfer of heat to the reactant gases. This transfer is also very advantageous in that the heating of gas to the plasma state requires less electric energy when residual heat from product cooling is employed to help heat the reactant gases into the plasma state.

When viewed as an integral unit the principal objective of the present invention is to fix nitrogen more efficiently in a plasma reactor by an effective and very short path heat transfer from reaction product to reactant gases to increase the yield of product fixed nitrogen and to reduce energy required to heat the reactants. To achieve the principal objective a subordinate objective is to increase the cooling rate over the cooling rates of the present art by providing large cooling surface in a small cooler which can directly intercept plasma state gases, and accordingly to cool the smaller cooler as simply and as effectively as possible without separate cooling fluids and cooling fluid pumps and pipes but rather to cool the same surfaces in the cooler which will be used to cool the plasma gases. This object then is to cool the cooler with reactant gases by using the same electrode as a reactant gas preheater. It can be stated conversely that an objective of the invention is to heat reactant gas prior to its entry into the plasma zone by heating the reactant gas heater with plasma effluent containing product to be cooled. Beside the heating of reactants and the cooling of products the invention seeks to control the energy density of the electric discharge by a control of the gas flow through the plasma region by drawing plasma gas into many ducts with narrow inside diameters and to thereby diffuse the plasma outward across a broad surface of electrode face.

An unexpected advantage is achieved by the present invention in virtue of the constant temperature fluctuations taking place on each electrode as it is repeatedly heated and cooled. In one embodiment these fluctuations are put to a further use of heating and cooling a catalytic coating placed on the heat exchanging surfaces of each electrode that contacts plasma gas. Then reactant gases absorbed at lower temperatures combine and products are desorbed at the higher temperatures in each fluctuation. An objective of this embodiment is to provide a repeating contact of the plasma state reactants onto catalytic surfaces of the electrodes which are cooling the plasma gases. The coatings are tungstic oxide and molybdenum oxide. These advantages and objectives will be clarified along with others by referring now to the drawings.

DETAILED DESCRIPTION OF DRAWINGS

Figure 1:
FIG. 1 of the drawings shows two small ducts or tubes with narrow inside diameters.
Figure 5:
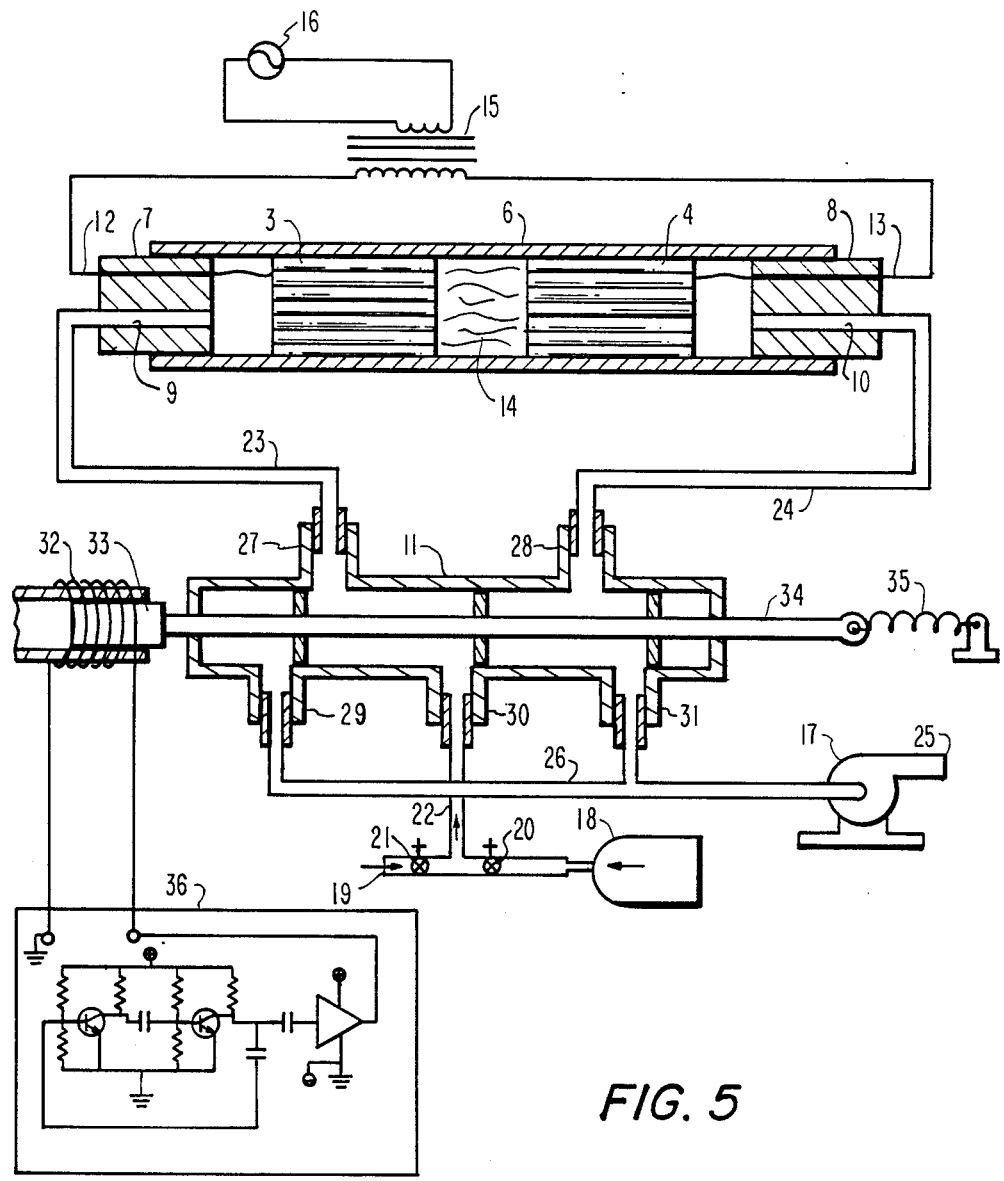
FIG. 5 shows a plasma chamber as in FIG. 4 but having additionally inlet and exit ports with gas transfer tubing connected to solenoid operated valving with the valving connected to a pump and to a gas source, the plasma chamber being also electrically connected by wires to a transformer.

Referring them to FIG. 1 of the drawings electrode elements 1 and 2 are metal tubes with small inside diameter and are capable of conducting heat from gas passing through them and over them. In one embodiment the electrode elements 1 and 2 are of tungsten metal the surface of which is oxidized with tungstic oxide to provide a heat transfer surface which is also a catalytic surface on which nitrogen and oxygen which are heated and activated in an adjacent plasma reactor to produce nitric oxide. Elements 1 and 2 conduct high voltage electric current from high voltage transformer terminals to produce an electric plasma arc between 1 and 2. The transformer and its terminals are shown in FIG. 5.

Figure 2:
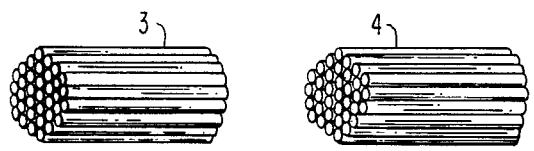
FIG. 2 of the drawings shows two clusters of ducts comprising many of the ducts shown in FIG. 1. Each of the two clusters is an electrode-heat exchanger.

Referring now to FIG. 2 electrodes 3 and 4 are comprised of clusters of elements 1 and 2 shown in FIG. 1. Electric current flows between 3 and 4 forming a plasma in the space between 3 and 4. All of the elements of electrode cluster 3 which each correspond to element 1 of FIG. 1 are in electric contact with each other. The same is true of the elements of 4 which each corespond to 2 of FIG. 1. Electrode cluster 3 is connected to one high voltage terminal of a transformer and electrode cluster 4 is connected to the other high voltage terminal of the transformer. The transformer and connections are shown in FIG. 5.

Figure 3:
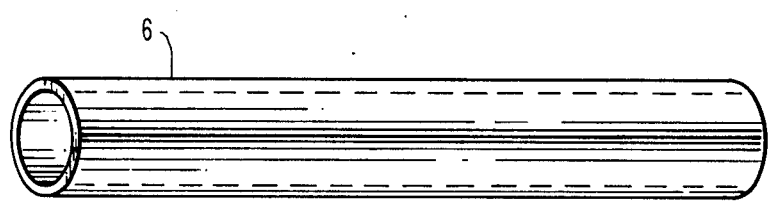
FIG. 3 shows a long cylindrical quartz tube which is a plasma chamber housing.

In FIG. 3 plasma chamber housing 6 is a hollow cylinder of high temperature resistant material such as quartz or alumina ceramic and it is capable of withstanding the high temperatures of a plasma.

Figure 4:
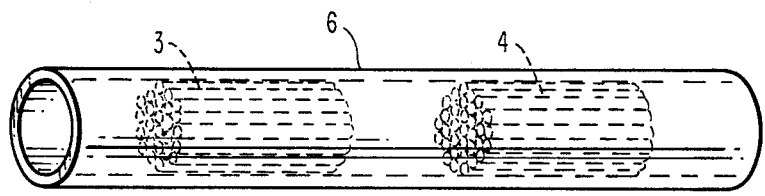
FIG. 4 shows the plasma chamber housing of FIG. 3 with two electrodes of tube clusters positioned inside the housing to form a plasma chamber.

In FIG. 4 the electrodes 3 and 4 described in FIG. 2 are shown inside of housing 6 shown in FIG. 3. The clusters 3 and 4 each fit tightly against the inner wall of 6 but are nevertheless moveable within 6 for the purpose of adjusting the separation distance between 3 and 4. In this way the separation between 3 and 4 is adjusted to the voltage applied across 3 and 4. For example when a voltage of approximatey 15 kilovolts is applied between these electrodes then they are separated by a space of approximately one inch and the plasma formed by the discharge between 3 and 4 will be about an inch in length.

In FIG. 5 the electrodes 3 and 4 are the same as in FIG. 4 as is plasma chamber housing 6. Plasma chamber seals 7 and 8 have gas passages 9 and 10 which conduct both reactant and product gases to and from valve 11 respectively. Seals 7 and 8 also have electric conduits 12 and 13 passing through them to bring high voltage current to electrode-heat exchangers 3 and 4 to form electric arc 14. Electric power transformer attached to power source 16 provides very high voltage to form the electric plasma 14 between electrodes 3 and 4. Vacuum pump 17 draws reactant gases from reactant gas reservoir 18 and from nitrogen inlet duct 19 through regulator valves 20 and 21 respectively. Then in a first time period, pump 17 drawes these reactant gases such as nitrogen and oxygen through duct 22 and valving 11 and through duct 23 into electrode 3 which preheats the reactants by heat transferred to 3 from 14. In the present condition of valve 11, reactants are drawn into plasma 14 and reacted to provide very hot equilibrium mixtures of products in the form of fixed nitrogen compounds and unreacted reactants which are cooled as they are drawn through 4. In one embodiment some or the hot unreacted reactants are reacted on the catalytic surfaces on the walls of 4 to increase the proportions of product gas as the mixture of product and unreacted reactant gases is being cooled in electrode 4. Fluid flow communication to product outlet port 25 of pump 17 is provided from 4 by gas passage 10, duct 24, valve 11 in its indicated condition and plenum duct 26 to pump 17. In a second and alternate condition of 11, shown later in FIG. 6, the flow of reactants is from electrode 4 through plasma 14 to electrode 3. In the second time period which corresponds to the second, alternate, condition of 11 fluid flow communication is from duct 22 then through 11 to 24 and 10, then into 4 and from 4 through 14 and then into 3. Then the flow is from 3 to 9 and 23, then back through 11 to 26 and 17 with the product again exiting at exit port 25. It should be noted that at the beginning of this second time period the electrode-heat exchanger 4 has been strongly heated by the gases flowing from 3 to 4 during the first period. Electrode 4 was heated as it was cooling the gases flowing into it from the plasma 14 during the first time period. However, it is equally important to note that simultaneously to the heating of 4 the electrode 3 is being cooled during the first period. Cool reactant gases are flowing through 3 during the first period. While it is true that the gases are being heated in 3 during the first period, nevertheless they are cooler than 3 and are cooling 3 while they are being heated by 3. At the end of the first period 3 has become relatively cool. At the beginning of the second period, since 3 has been cooled, it is capable of cooling gases that are now coming to 3 from 4 and through the hot plasma 14. Consequently, in the second period the roles of 3 and 4 are changed simply by a change in the condition of valving 11. Heat from the plasma has been transferred to the reactant gas to preheat the reactants and to freeze the equilibrium of the products in the plasma and all of this is accomplished by an alternation in the direction of flow between 3 and 4. Subsequent reversal of flow from 4 to 3 achieves the same effect because, at the end of the second period, when 3 has been heated by the flow into it from the plasma which it has been cooling, then 4 has been cooled by the reactants it has been heating. Since 3 is very hot and 4 cooled at the end of the second period, reversal of flow at that time will enable reactants to be preheated by 3 as they were in the first period and it will also enable the product from 14 to be cooled in 4 as they were in the first period. Accordingly, the third period corresponds to the first period and a fourth period will correspond to the second period and so on. The function of 3 in one period is the same as the function of 4 in the next period and the function of 4 in one period is the same as that of 3 in the next period with the result that in each of the two possible conditions of valve 11 product cooling is taking place as is reactant preheating. Similarly, product cooling is always occurring irrespective of which of two possible directions flow is taking place through the plasma zone. The same is true of reactant preheating. Heating of reactants and freezing of proportions of products is always occurring immediately adjacent to the plasma reaction zone 14 to provide the quickest and most effective heat transfer. Because the functions of 3 and 4 are continually and repeatedly being exchanged from one period to the next in every embodiment of the basic inventive concept, then in the particular embodiment in which a catalytic surface is employed on the surface of one electrode for its effects while the plasma is being cooled, it is also used on the opposite electrode for the catlaytic effects while that opposite electrode is effecting the cooling of the plasma gas. In the embodiment mentioned in which 4 is of tungsten tubes and they have a tungstic oxide coating then the composition of 3 is the same. In the embodiment shown in this FIG. 5 the valving 11 is a spool valve with five ports and two possible conditions. The ports are ports 27, 28, 29, 30 and 31. The first condition consists of two separate fluid flow communications, namely a fluid flow between 27 and 30 and a fluid flow between 28 and 31. The second condition consists of two separate fluid flow communications, namely a fluid flow between 27 and 29 and a fluid flow between 28 and 30 only. The valve 11 is alternated between its two conditions by solenoid 32 acting magnetically on plunger 33 which is connected to valve rod 34. Variable frequency power oscillator 36 periodically and repeatedly energizes 32 pulling 33 to the left, moving 34 leftward and tensioning spring 35 thereby moving 11 to the condition shown later in FIG. 6. In one embodiment 36 is an astable multivibrator of controllable frequency capable of providing an approximately square wave form with equal periods of output current and no output current so that there will be an equal amount of time in each full cycle when 33 is pulled to the left as when spring 35 pulls it to the right. It is not intended to limit the inventive concept to any single type of timing oscillator or timer, but rotory switches with commutators may be used or relay logic with flip-flop circuits and time delay capacitors may be employed as well as other types of repeating interrupter circuits that are well known in the art. Similarly, it is not intended to limit the inventive concept to any particular type of valve to achieve the valving conditions that are represented by valve 11. Any valving system capable of reversing the direction of flow through the plasma zone 14 is acceptable according to the operating principle of the invention provided only that flow is toward and into the plasma chamber from the source of reactants and that any flow moving from the plasma is caused to move to a product output port such as port 25.

Figure 6:
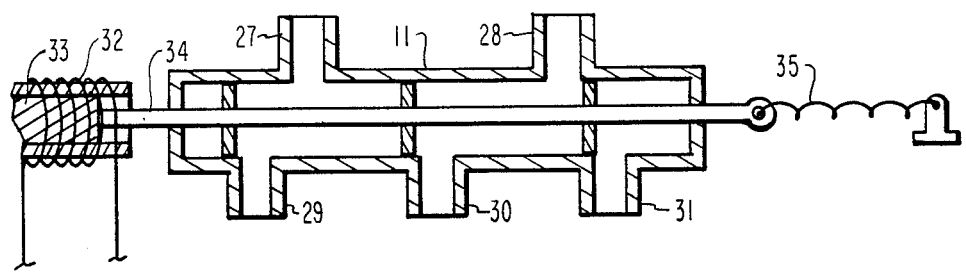
FIG. 6 of the drawings shows the solenoid operated valving of FIG. 5 in an alternate condition to the condition of FIG. 5.

In FIG. 6 the valve 11, which was shown in FIG. 5 in one condition, is shown in its alternate condition providing fluid flow communication between ports 27 and 29 and another fluid flow communication between ports 28 and 30. This condition is achieved when solenoid 32 is energized and plunger 33 is drawn into 32 moving valve rod 34 to the left tensioning spring 35. The other connections to 11 are shown in FIG. 5 and are not repeated in this FIG. 6.

Figure 7:
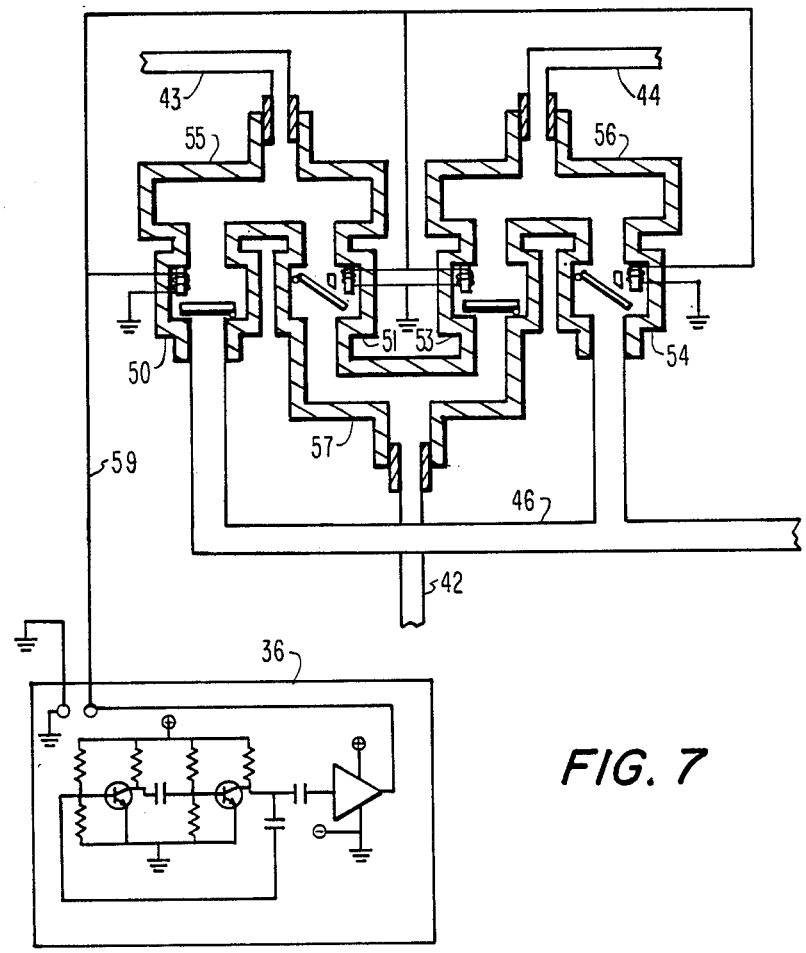
FIG. 7 shows a network of four electric valves with three plenums and five connecting ducts with the valves being driven by an astable multivibrator.

Referring then to FIG. 7 the valves 50, 51, 53 and 54 function together to perform the same alternation in fluid flow communication that valve 11 in FIG. 5 performs. In this FIG. 7 duct 43 corresponds to duct 23 in FIG. 5 and connects the valving network of valves 50, 51, 53 and 54 to plasma chamber seal 7. Similarily, duct 44 in this FIG. 7 is the same as 24 in FIG. 5 and connects the same network to plasma chamber seal 8. Duct 42 connects the network of valves in this FIG. 7 to the reactants 18 and 19 as shown in FIG. 5 and serves the same purpose as duct 22 in FIG. 5. In this FIG. 7 the plenum chamber 57 provid provides fluid flow communication between 42 and valves 51 and 53. Plenum 55 provides fluid communication between duct 43 and valves 50 and 51. Similarly, plenum 56 provides fluid flow between duct 44 and valves 53 and 54. Valves 51 and 54 are normally open and provide flow-through when not energized, while valves 50 and 53 are normally closed valves and prevent flow-through when not energized. The periodic, intermittent flow of electric current opens 50 and 53 and closes 51 and 54. During alternate periods of equal time duration the the absence of current opens 51 and 54 and closes 50 and 53. Reacted gases containing combined nitrogen products flow through duct 46 to vacuum pump 17 just as they do through duct 26 in FIG. 5. Pump 17 is not shown in this FIG. 7 because its function is described in FIG. 5. The power oscillator 36 functions in the same way that it does in FIG. 5 and provides a wide range of selectable frequencies. On a frequency selected 36 provides periodic flows of electric current and these flows alternate with periods of equal duration in which no current is flowing. The output of 36 is electrically connected by electric harness 59 to the electric valves 50, 51, 53 and 54 to produce the proper alternation in the condition of the valve network to repeatedly reverse the gas flow through plasma chamber 11 to which the network is connected.

Throughout the drawings particular voltages and electrode separation distances have not been assigned because a wide variation is possible according to the basic operating principle. For instance, in FIG. 5 a large separation of several inches is useful when the high voltage transformer 15 is a transformer of the type used to power large X ray tubes and provides 100 KV., but the separation distance of only a quarter of an inch is appropriate between 3 and 4 when the arc has only 6000 volts across it. The diameter of the electrode cluster which comprises electrodes 3 and 4 also admits of design variation depending upon the current flow through the plasma. When high amperage plasmas are employed and the plasma is exceptionally thick and hot, then it is appropriate to employ an electric cluster of relatively large diameter. Variations in design of electrode separation and thickness are also dependent upon the intensity of the vacuum or on the pressure of the gases in the plasma zone. In the embodiment in which the pressure in the plasma zone 14 is one sixth of an atmosphere the separation of the electrodes 3 and 4 can be as much as three inches when the voltage is 15 kilovolts across the electrodes, while less separation still provides satisfactory operation. A small X ray transformer of 35 KV used in another embodiment produces a strong active plasma with a separation distance between 3 and 4 of two inches when the gas pressure is approximately one atmosphere. It is not intended to limit the basic inventive concept to electrode elements that have certain specified dimensions because it is clear that when a plasma of relatively high energy is employed, it is advantageous to have a relatively high flow rate of gas through the plasma in order to react a relatively larger quantity of gas in a given time. This situation dictates the use of larger surface area in the heat exchanger to provide adequate rapid cooling of product and heating of reactant. To achieve maximum energy efficiency the maximum amount of heat is exchanged between products and reactants and longer electrode elements are employed for heat absorbtion and release. Since it is well known in the art that the shape and form of many kinds of electric arcs can be easily distorted by a draft of air or other gas through the arc, one embodiment of the invention employs a higher velocity but low volume gas flow through the plasma by using very small inside diameter electrode elements to cause the arc to be fanned out and pulled through many thin electrode elements thus providing a more diffuse plasma and a more rapid cooling of it.

The rate of the reversal of gas flow through the plasma depends upon the energy of the plasma, the flow rate through the plasma of the gas and the rate at which heat is absorbed and released by the heat exchanging electrodes. Another significant variable in determining the rate or reversal of gas flow through the plasma is the the gas pressure of the plasma zone. When a high vacuum is employed in the plasma there is much less quantity of gas flowing for a given rate of flow through the zone than when the reacting gas is flowing at atmospheric pressure. When the quantity is less at a given rate of flow, there is less heat to be transferred in a given time and the reversal rate can be slower, if other things are equal. Because there are so many variable factors involved in the determination of the reversal rate for achieving either optimum energy efficiency or optimum yield per unit of time, the principle embodiment of the inventive concept employs a variable rate electric oscillator capable of stable, single frequency oscillation on any frequency from one cycle per minite to several cycles a second, and the optimum rate for a particular reactor using particular voltages and amperages in a reactor of a particular size is determined experimentally by employing a variety of reversal rates and measuring product yield and the energy consumed during the time a particular frequency is being applied for control of reversal rate.

The reactant gases employed in the basic embodiment are nitrogen and oxygen and the proportions are stoichiometric and the product is nitric oxide. Other useable proportions are those found in air in one embodiment and in another two parts of oxygen are used for every part of nitrogen, but the invention is not limited to any particular proportions of reactants. Other reactant gases to be reacted according to the present inventive concept are nitrogen and hydrogen to provide ammonia and hydrazine, and this reaction is best achieved in a very mild plasma at relatively high flow rates. The invention is able to effect other combinations besides those involving nitrogen such as the partial oxidation of methane to methanol when one oxygen atom or less is present in the reactor for each molecule of methane and the electric plasma is very mild, employing just enough current to sustain a visible discharge. In this embodiment methane is admitted through inlet duct 19 in FIG. 5 in place of nitrogen and a very limited flow of oxygen is admitted from reservoir 19.

While the drawings show an alternating current source for high voltage electric discharge as indicated by the transformer 15 of FIG. 5, nevertheless, it is not intended to limit the inventive concept to alternating current and direct current, high voltage is employed in some embodiments, but it is not shown as it is well understood how to generate high voltage direct current.

I claim:

1. A gas phase chemical reactor having gas heating and excitation means in the form of an high voltage electric discharge between two electrodes and through reacting gas, said reactor comprising two gas ducting electrodes, each in the form of a cluster of metal tubes, each tube of the cluster conducting gas to and from the plasma and transferring heat energy to and from the gas it is carrying, each electrode for contacting the plasma and for alternately first removing and cooling plasma heated gas product while the other electrode is heating reactant gas and injecting it into the plasma, and then, after gas flow direction reversal, for heating and injecting reactant gases into the plasma while the other electrode is removing and cooling plasma heated gas product;

an high temperature, heat resistant housing being sealed on either end by seals having 9 as and electric conduit ports and enclosing said electrodes and said plasma within in such a manner that said housing provides series fluid flow communication through one electrode, the plasma and the other electrode, and gas flow direction reversal means in the form of electric valving and automatic valve repeated actuating means, said valving being capable of receiving a flow of reactant gases from a source by ducting and then of periodically and repeatedly reversing the direction of flow through said housing and of then directing the flow from said housing through ducting to a product output port, and reactant and product gas circulation means in the form of a vacuum/pressure pump capable of moving gas from a source, through said valving for repeatedly reversing flow direction, through the plasma housing and again through said valving and to an output duct.

2. A gas phase chemical reactor as in claim 1 in which the electric valving and automatic valve repeated actuating means is a solenoid actuated spool valve having three spools, the valve being capable of two conditions with each of the two separate conditions providing two separate fluid paths each of which paths is the result of a selection between two possible alternate ports and a third common port in one condition one of the two separate paths being capable of providing a fluid flow between a reactant gas inlet port and a left side of said plasma housing while the other separate path provides fluid flow between a product outlet port and the right side of a plasma housing, and in the alternate valve condition, the separate paths being reversed, one path being capable of providing fluid flow between a product inlet port and a right side of the plasma housing while the other path is capable of providing fluid flow between a product outlet port and a left side of the plasma housing, and in which the automatic valve repeated actuating means is a power oscillator in the form of an astable multivibrator capable of repeatedly and intermittently providing periods of power to actuate the valve solenoid followed by equal length periods of no power to deenergize the the solenoid.

3. A gas phase chemical reactor as in claim 1 in which the electric valving and automatic valve repeated actuating means is in the form of a network of four electric valves, two normally open valves and two normally closed valves, the two normally open valves being open together to provide one condition of the network and two separate fluid flow paths and the two normally closed valves being open at an alternate period to provide an alternate valve network condition and two different separate flow paths, the normally open valves being closed when the normally closed valves are open, and the normally closed valves being closed when the normally open valves are open; in one network condition one of the normally open valves being open and providing a fluid flow between a reactant gas inlet port and the left side of said plasma housing while the other normally open valve is open and providing fluid flow between a product outlet port and the right side of the plasma housing, and in the alternate valve network condition effected by a flow of electric current to each valve, the normally closed valves being open, one of the normally closed valves providing fluid flow between a reactant gas inlet port and the right side of said plasma housing while the other normally closed valve now open is providing fluid flow between a product outlet port and the left side of the plasma housing, and in which the automatic valve repeated actuating means is a power oscillator in the form of an astable multivibrator having its power output connected in parallel to each valve of the network and being capable of repeatedly and intermittently providing periods of power to actuate the electric valves followed by equal length durations of no power for deenergizing the electric valves.

4. A gas phase chemical reactor as in claim 1 in which the two clusters of tubes, that are the electrodes capable of ducting reactant and product gas, are composed of tungsten tubes the surface of which is oxidized to tungsten oxide and are capable of providing catalytic action on the gas reactants of the plasma which are nitrogen and oxygen and assisting the plasma reaction in the production of nitric oxide.

5. A gas phase chemical reactor as in claim 1 in which the reacting gases are nitrogen and oxygen and the product of the reaction is nitric oxide.

6. A gas phase chemical reactor as in claim 1 in which the reacting gases are nitrogen and hydrogen and the product is ammonia.

7. A gas phase chemical reactor as in claim 1 in which the reacting gases are methane and oxygen and the product is methanol.

8. A gas phase chemical reactor as in claim 1 in which the automatic valve repeated actuating means is a rotary switch with commutators periodically making and breaking an electric current to electric valves.

9. A gas phase chemical reactor as in claim 1 in which the two clusters of metal tubes, which function as electrodes, gas ducts and heat exchangers, are coated with molybdenum oxide and are thereby capable of providing catalytic action to assist in reacting the gas reactants of the plasma which contacts the electrodes and of increasing the yield of combined nitrogen product, the reactants being nitrogen and oxygen and the product being nitric oxide.

* * * * *